(12) United States Patent
Sühling et al.

(10) Patent No.: US 8,184,884 B2
(45) Date of Patent: May 22, 2012

(54) METHOD FOR EVALUATING A TOMOGRAPHY DATA RECORD, AND A TOMOGRAPHY WORKSTATION

(75) Inventors: Michael Sühling, Erlangen (DE); Matthias Thorn, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1028 days.

(21) Appl. No.: 12/155,050

(22) Filed: May 29, 2008

(65) Prior Publication Data

US 2009/0022261 A1    Jan. 22, 2009

(30) Foreign Application Priority Data

May 31, 2007  (DE) .......................... 10 2007 025 401

(51) Int. Cl.
*H05G 1/60* (2006.01)
(52) U.S. Cl. ............................................ 382/131; 378/4
(58) Field of Classification Search ................ 378/4–20, 378/901; 382/128, 131
See application file for complete search history.

(56) References Cited

U.S. PATENT DOCUMENTS

| | | | |
|---|---|---|---|
| 6,785,410 B2 | 8/2004 | Vining et al. | |
| 2005/0078859 A1 | 4/2005 | Cathier | |
| 2005/0135662 A1* | 6/2005 | Vining et al. | 382/128 |
| 2006/0155579 A1 | 7/2006 | Reid | |
| 2006/0182328 A1 | 8/2006 | Guendel | |

FOREIGN PATENT DOCUMENTS

| | | |
|---|---|---|
| DE | 102004060931 A1 | 7/2006 |
| DE | 102006000713 A1 | 7/2006 |
| WO | WO 03046810 A1 | 6/2003 |
| WO | WO 2005031648 A2 | 4/2005 |

OTHER PUBLICATIONS

German Office Action Mar. 11, 2008.

* cited by examiner

*Primary Examiner* — Hoon Song
(74) *Attorney, Agent, or Firm* — Harness, Dickey & Pierce, P.L.C.

(57) ABSTRACT

A method is described for evaluating a tomography data record. In at least one embodiment, a tomography data record of a hollow organ is generated, the tomography data record is analyzed automatically, and organ sections to be assessed as critical are determined. Further, a corresponding findings list entry is generated in a findings list as a reaction to a determined organ section to be assessed as critical, various organ sections are displayed successively on the basis of the tomography data record, and after its first display, an organ section assessed as critical can be selected for renewed display directly via the findings list. Furthermore, a corresponding tomography workstation is described.

17 Claims, 2 Drawing Sheets

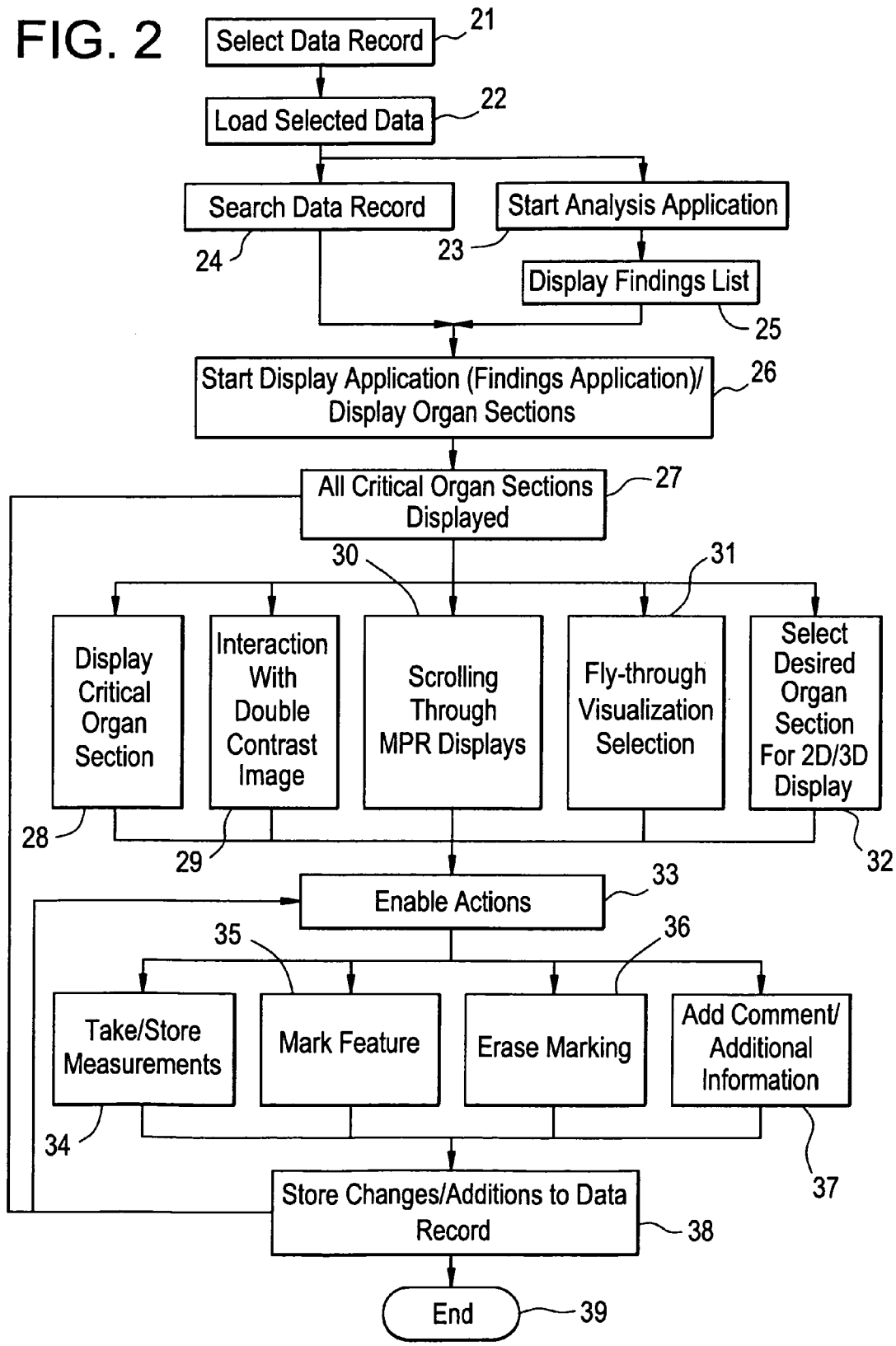

METHOD FOR EVALUATING A TOMOGRAPHY DATA RECORD, AND A TOMOGRAPHY WORKSTATION

PRIORITY STATEMENT

The present application hereby claims priority under 35 U.S.C. §119 on German patent application number DE 10 2007 025 401.8 filed May 31, 2007, the entire contents of which is hereby incorporated herein by reference.

FIELD

Embodiments of the invention generally relate to a method for evaluating a tomography data record of a hollow organ. In at least one embodiment, such hollow organs can include but are not limited to a stomach, an intestine, a windpipe, a blood vessel or a lung. Embodiments of the invention further generally relate to a corresponding tomography workstation; for example they may relate to a computed tomography workstation or a magnetic resonance tomography workstation.

BACKGROUND

The diagnostic access to diseases of the intestine is subjected to constant change as a consequence of advances in medical technology.

Endoscopic methods for a long time constituted the standard for intestinal diagnostics. Since, because of their invasive nature, the endoscopic methods are rejected by a portion of the patients, in particular as regards preventive diagnostics, non-invasive diagnostic methods based on imaging are currently becoming established.

Modern radiological sectional imaging methods such as computed tomography and NMR tomography for acquiring appropriate tomography data records (single slice data records or volume data records) and reconstruction methods based on these data enable non-invasive diagnostic techniques, for example of the intestine.

It is known to display such tomography data graphically in various ways. For example, the following forms of display are known for tomography data:

The classic view in the transverse 2D reconstruction.

A volume rendering mode as 3D method ensures an opaque "inspection" through the colon loops.

Virtual endoscopy. This concerns a 3D reconstruction method in which the inner surface of hollow organs is displayed in the sense of an endoluminal view. This enables even the "inner" surface of hollow organs, in particular the intestinal surface, to be displayed virtually. This technique is applied, for example, in virtual endoscopy of the colon and, because of the high resolution that can be attained, even permits the detection of very small colon polyps from which colorectal carcinomas result according to the current state of knowledge. Detecting these polyps early can prevent the development of carcinoma.

Moreover, a method for automatic computer-aided detection (CAD) of colon polyps based on a tomography data record is known per se, for example from WO 2005/031648 A2 (EP 1665163 A2). The field of application of the innovative computer-aided detection (CAD) will spread substantially in the coming years.

SUMMARY

In at least one embodiment of the invention, a technical teaching is specified that enables a tomography data record to be evaluated quickly and reliably.

At least one embodiment of the invention is based firstly on the idea that after the generation of the tomography data record, for example a set of tomographic images, and, as a rule, before the display, based on the tomography data record, of organ sections, the tomography data record is analyzed automatically and organ sections to be assessed as critical are determined and retained.

Consequently, the time interval between the generation of the tomography data record and the display, based thereon, of organ sections is used for automatic analysis. This permits a user (person making the findings or radiologist) to offer or indicate at the same time as the display of organ sections further information resulting from the automatic analysis, in particular a CAD.

It is thereby possible to evaluate the tomography data record reliably and comprehensively by using the results of the automatic analysis. As a rule, the user need no longer wait for the termination of the computationally intensive automatic CAD analysis.

For example, an analysis of the tomography data record, an automatic determination of organ sections to be assessed as critical, and a generation of a corresponding findings list entry in a findings list are carried out automatically, in particular as an analysis application, before—particularly in the course of a display application or findings application—the organ sections are displayed on the basis of the tomography data record, particularly in a fashion initiated and/or selected by a user.

In at least one embodiment, it is preferred firstly to generate a tomography data record of a hollow organ. A tomography data record generally includes a volume data record, a 3D data record, a 2D data record and/or a multiplicity of slice data records or data based thereon, for example image data in various processing stages.

The tomography data record is then analyzed automatically, for example by computer-based image recognition methods or pattern recognition methods, and organ sections to be assessed as critical are determined. An organ section is, for example, to be assessed as critical when the tomography data assigned to this organ section indicate irregularities or striking features with regard to the shape, the brightness profile or the color profile that point to a lesion, an overgrowth or a polyp.

A corresponding findings list entry is generated in a findings list as a reaction to a determined organ section to be assessed as critical. In this case, the corresponding findings list entry is, for example, assigned a data pointer referring to the corresponding tomography data.

Various organ sections are then displayed successively on the basis of the tomography data record, in particular in a two-dimensional sectional display and/or in a virtual perspective display (virtual three-dimensional display).

An organ section to be assessed as critical initially (directly after the beginning of the display of organ sections) cannot be selected for display directly via the findings list, but can be selected for renewed display directly via the findings list only after its, or with its, in particular, first-time display. The first-time display of an organ section is in this case initiated or selected by a user, in particular.

Thus, the automatically generated findings list entry corresponding to a critical organ section is not released for a direct navigation to the associated organ section, in particular for displaying the associated organ section, until the display of the associated organ section has already previously taken place, in particular at the prompting of the user. Before a first-time display of an organ section, its display cannot be initiated via the findings list; the corresponding findings list entry is blocked.

To this end, an organ section displayed at least once, or the corresponding tomography data are recorded as "displayed", for example. A findings list entry whose associated organ section or whose corresponding tomography data are recorded as "displayed" can then, for example, be selected by a mouse click on the corresponding findings list entry in a graphical display of the findings list, in order to initiate the display of the associated organ section.

It is thereby ensured that not only can an evaluation of the tomography data be reduced to automatically determined critical organ sections (by direct navigation to these organ sections), but that as a rule all or at least a large portion of the organ sections are necessarily indicated previously by the user.

The necessary, and thus also documented viewing at least of a majority of the organ sections by a user can, in some countries, also have legally advantageous effects, for example whenever it is prescribed by appropriate guidelines that a doctor or radiologist must act as first finder of the tomography data.

Thus, owing to at least one embodiment of the invention the reliable and, if appropriate, legally advantageous display, effected by the user, at least of a majority of the organ sections is coupled to the automatic analysis of the tomography data in such a way as overall to enable an evaluation of the tomography data quickly and reliably. In addition, via the findings list the user is enabled to make a quick and comfortable initiation of a renewed display of a critical organ section.

It is preferably provided that the findings list is displayed at least partially during the, particularly also first-time, display of the organ sections. This display of the findings list takes place, for example, in a fashion superposed on the display of the organ sections, or in another window or display.

Thereby, as early as during the first-time display of organ sections, a user obtains results based on the automatic analysis, for example, with regard to the number of the critical organ sections that substantially corresponds to the number of the findings list entries, or with regard to the relevance of the critical organ sections, which can form a part of a findings list entry.

The display of a findings list entry advantageously takes place after or with the first display of the corresponding organ section in a highlighted fashion, for example with color marking, in a larger or underlined fashion, etc. As a result, the release of a findings list entry for direct navigation to the associated organ section is indicated at once to a user.

The organ sections to be displayed are preferably selected manually for, in particular, first-time display by the user, for example via an appropriate input device, in order manually to navigate through the displays of the organ sections, to scroll, to leaf or to "fly" virtually.

A preferred refinement of at least one embodiment provides that a findings list entry includes a reference to a critical organ section, to corresponding tomography data, to corresponding image data and/or to, corresponding findings data such as polyp shape, polyp size, polyp relevance or polyp position within the organ section, etc. In particular, the findings data can be displayed at least partially as part of the findings list entry. The evaluation of the tomography data is thereby facilitated.

In order further to support the user during the evaluation in the case of the first and/or renewed display of a critical organ section, the site of the organ section that is causal for the critical assessment is highlighted, for example framed, automatically.

In order to ensure a complete and reliable evaluation of the tomography data, it is advantageously provided that it is checked automatically before termination, in particular initiated manually via the input device by the user, of the display of organ sections or of the display application/findings application whether the fraction of the displayed organ sections relative to the displayable organ sections exceeds a prescribed threshold value, and that an optical or acoustic reference signal or a reference message is output when the fraction of the displayed organ sections relative to the displayable organ sections does not exceed a prescribed threshold value of, for example, 90%.

Alternatively, or in addition thereto, it is provided that it is checked automatically before termination, in particular initiated manually by the user, of the display of organ sections or of the display application/findings application whether all organ sections assessed as critical have been displayed, and that an optical or acoustic reference signal or a reference message is output when not all organ sections assessed as critical have been displayed.

In at least one embodiment, a tomography workstation is disclosed having an interface for receiving tomography data records, having an output interface to an output device such as a graphic display, having an input interface to an input device, and having a computing device.

The computing device, which can include a processor and storage devices, may be set up, in at least one embodiment, in programming terms in such a way that a tomography data record obtained via the interface is analyzed automatically, and organ sections to be assessed as critical are determined, that a corresponding findings list entry is generated in a findings list as a reaction to a determined organ section to be assessed as critical (for example, in a logic memory section provided therefor), that various organ sections are displayed successively on the output device via the output interface on the basis of the tomography data record, and that after its first display, which was triggered, in particular, by control commands obtained via the input interface of the input device, an organ section assessed as critical can be selected for renewed display directly via the findings list.

The tomography workstation, in at least one embodiment, can be a workstation that is directly connected to a tomography machine and can, for example, also be used to control the tomography machine. However, it can also be a separate workstation for analyzing and further processing tomography data records that is connected to one or more tomography machines, for example via a network, in particular via a radiological information system.

BRIEF DESCRIPTION OF THE DRAWINGS

The invention is explained in more detail below with the aid of example embodiments and with reference to the attached figures, in which:

FIG. 2 shows a simplified flowchart of a method for evaluating tomography data.

DETAILED DESCRIPTION OF THE EXAMPLE EMBODIMENTS

Figure 1:
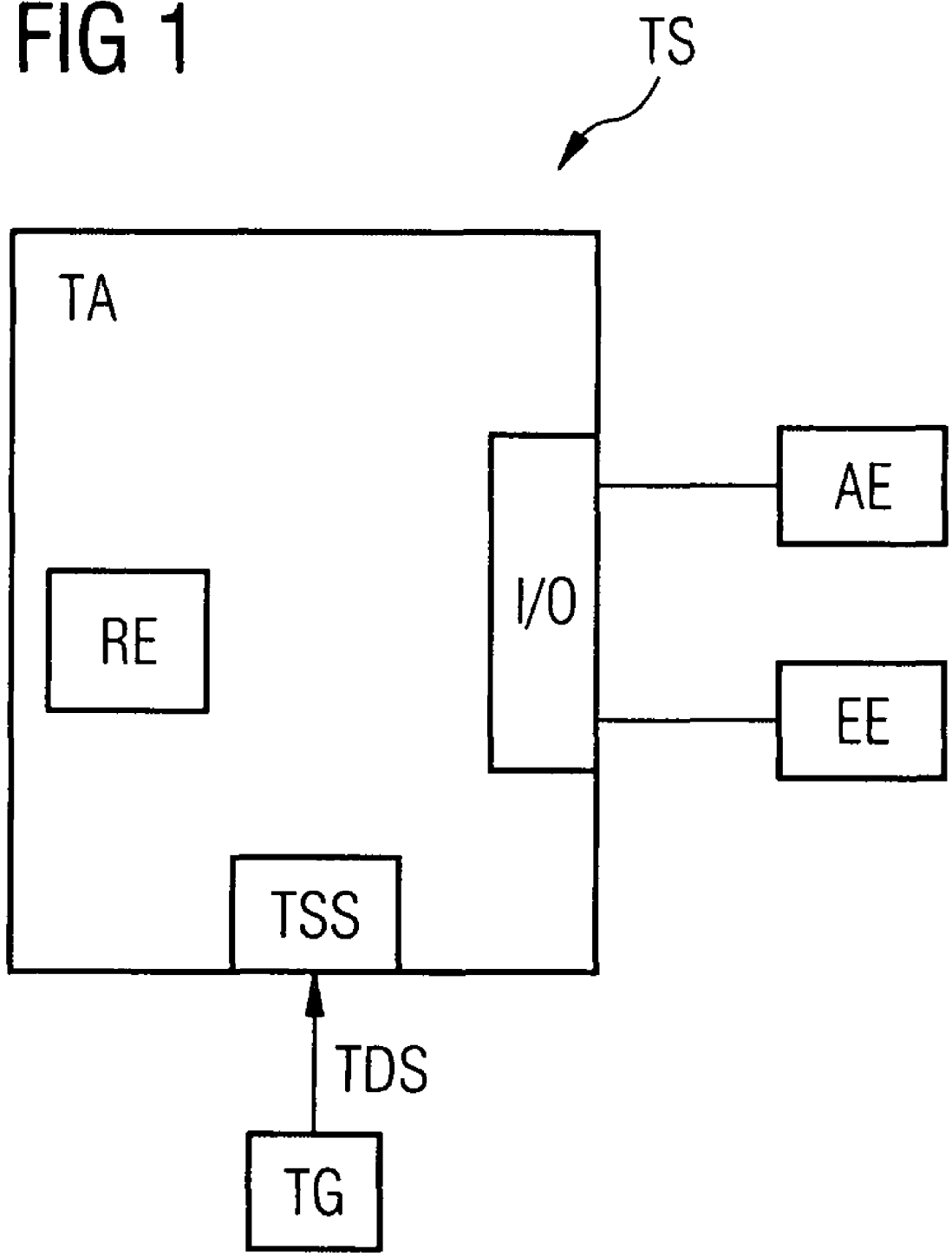
FIG. 1 shows a simplified block diagram of a tomography system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 illustrates a tomography workstation TA having a computing device RE that can include a processor device and storage devices, which workstation is—without restriction of generality—directly a component of a tomography system TS. Here, a tomography machine TG such as a computed tomography machine, is driven by the tomography workstation TA via a tomography interface TSS. Tomography data TDS are transmitted to the tomography workstation TA via the tomography interface TSS from the tomography machine TG. Alternatively, the workstation could also be a remote one that is connected to the tomography system via a network by means of an interface.

Information is exchanged between the tomography workstation TA and a display device AE or an input device EE via an input/output interface I/O.

On the basis of a tomography data record TDS, images are displayed on the display device AE, for example a graphic display.

The tomography workstation TA and the tomography machine TG are driven via the input device EE, such as a keyboard or a computer mouse. For example, the cycle, explained further below of a method for evaluating tomography data can be influenced via the input device EE.

The processor device is set up in programming terms in such a way that it is possible in accordance with the following method, explained with the aid of FIG. 2, for evaluating tomography data, to evaluate a tomography data record TDS generated by a tomography machine TG.

In a first step (not illustrated), a tomography machine firstly generates a tomography data record that describes a hollow organ such as, for example, the intestine or the lung of a patient, and transmits it to the tomography workstation.

After complete transmission of the data, the evaluation application is started in step 21, and a user is requested to select a tomography data record or a part of a tomography data record.

After the data selected by a user have been loaded in step 22, in step 23 an analysis application is automatically started by means of which the loaded and, optionally, conditioned tomography data record is examined on the basis of CAD (computer-aided detection) methods known per se for critical organ sections that probably contain a colon polyp.

Organ sections assessed as critical are entered in a findings list. A findings list entry includes a pointer to the corresponding data of the tomography data record, and a description of the findings such as, for example, the extent of the findings, the type of findings or a measure of the probability that these findings are to be assessed as critical.

As an alternative to this, it is possible (not illustrated) that the analysis application is started automatically after the complete transmission of the data from the tomography machine to the tomography workstation, if appropriate after conditioning or preprocessing of the tomography data record. The selection of a data record and its corresponding loading takes place in this case after the transmission of the data record, likewise automatically.

At the same time as step 23, in step 24 an automatic search is made in the tomography data record for the portion of the data that represents the starting position in the intestine.

After termination of the CAD method, the findings list is displayed as its result in step 25. Said list specifies the number of the organ sections automatically assessed as critical, refers in terms of data to the corresponding organ sections or to the corresponding data, and describes each individual organ section assessed as critical, or the corresponding findings.

The display application (findings application) is then started. On the basis of the tomography data record, in step 26 the organ sections are displayed, in a way known per se in sectional images and/or in a virtual three-dimensional display via the input device in a fashion initiated or selected by a user.

The display of the organ sections can take place beside one another in various views. For example, in two upper display windows of a display device, the MPR (Multiplanar Reconstruction) view (coronal and sagital) can be displayed, a global view of the entire hollow organ can be displayed bottom left, and the virtual three-dimensional (endoluminal) view can be displayed bottom right.

The findings list entries are, for example, initially illustrated without being underscored in black font in a fashion superposed on the display of the organ sections. A selection of a findings list entry for direct navigation cannot be made by the user via the input device, since the findings list entries have not yet been cleared.

Not until the display, initiated by the user, of an organ section assessed as critical by the CAD method, is the associated findings list entry for direct navigation cleared. This is signaled by displaying the corresponding display of the findings list entry by underscoring, for example, and in red. This findings list entry can now, for example, be selected by the user by "clicking" with the computer mouse in order to effect an immediate display of the corresponding critical organ section.

Once all the critical organ sections initiated at least once by the user have been displayed, the system permits or enables the following actions for a user starting from a release step 27:

Action 28: Jumping directly to a display of a critical organ section by selecting the corresponding findings list entry (just explained).

Action 29: Interaction with a so-called double contrast image.

Action 30: Scrolling or leafing through MPR displays.

Action 31: "Flying" virtually through the virtual three-dimensional display ("fly through visualization").

Action 32: Selecting a desired organ section for a two-dimensional or three-dimensional display, in order to place the virtual endoscope at any desired site of the virtual hollow organ.

Starting from actions 28 to 32, the system permits or enables the following actions for the user starting from a release step 33:

Action 34: Measurements particularly regarding the size of polyps, striking features or lesions can be undertaken and stored, particularly in the MPR display.

Action 35: By way of the input device, the user can mark a striking feature within a particularly critical organ section. This mark is then also visible in the remaining views. A new findings list entry that refers to an organ section just displayed can likewise be compiled.

Action 36: By way of the input device, the user can erase a findings marking. A findings list entry that, for example, results from the automatically carried out CAD method and is assessed as uncritical by the user can likewise be erased.

Action 37: By way of the input device, the user can add to the findings list entry a comment or additional information that describe the striking feature in more detail.

Starting from actions 34 to 37, in step 38 changes or additions undertaken can be stored as part of the tomography data record or as a file assigned to the tomography data record.

After such storage or buffering, the method can be continued with step 27 or 33, or be ultimately ended in step 39.

It may be pointed out once again explicitly at this juncture that the figures merely illustrate examples. In addition to the components illustrated, the tomography system can include any further desired components. Likewise, the cycle of the evaluation method explained can have further steps over and above the steps illustrated, or provide the steps illustrated in another sequence.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for evaluating a tomography data record, comprising:
    generating a tomography data record of a hollow organ;
    automatically analyzing the tomography data record and determining organ sections to be assessed as critical;

generating a corresponding findings list entry in a findings list upon determining an organ section to be assessed as critical;

successively displaying various organ sections on the basis of the generated tomography data record; and rendering an organ section assessed as critical, after first display, as selectable for renewed display directly via the findings list.

2. The method as claimed in claim 1, wherein the findings list is displayed during the display of the organ sections.

3. The method as claimed in claim 1, wherein the display of a findings list entry takes place in highlighted fashion after the first display of the corresponding organ section.

4. The method as claimed in claim 1, wherein the organ sections to be displayed are manually selectable by a user.

5. The method as claimed in claim 1, wherein a findings list entry includes a reference at least one of to an organ section, to corresponding tomography data, to corresponding image data and to corresponding findings data.

6. The method as claimed in claim 1, wherein, during the display of a critical organ section, a site of the organ section that is causal for the critical assessment is highlighted automatically.

7. The method as claimed in claim 1, further comprising:

determining, before termination of the display of organ sections, whether the fraction of the displayed organ sections relative to the displayable organ sections exceeds a threshold value; and outputting a reference signal when the fraction of the displayed organ sections relative to the displayable organ sections does not exceed the threshold value.

8. The method as claimed in claim 1, further comprising:

determining, before termination of the display of organ sections, whether all organ sections assessed as critical have been displayed; and outputting a reference signal when not all organ sections assessed as critical have been displayed.

9. A tomography workstation, comprising:

an interface for receiving tomography data records;

an output interface to an output device;

an input interface to an input device; and a computing device, set up in such a way that a tomography data record, obtained via the interface, is analyzed automatically, and organ sections to be assessed as critical are determined, a corresponding findings list entry is generated in a findings list as a reaction to a determined organ section to be assessed as critical, various organ sections are displayed successively on the output device via the output interface on the basis of the tomography data record, and after first display, an organ section assessed as critical is selectable for renewed display directly via the findings list.

10. The tomography workstation as claimed in claim 9, wherein the findings list is displayed during the display of the organ sections.

11. The tomography workstation as claimed in claim 9, wherein the display of a findings list entry takes place in highlighted fashion after the first display of the corresponding organ section.

12. The tomography workstation as claimed in claim 9, wherein the organ sections to be displayed are manually selectable by a user.

13. A tomography workstation for evaluating a tomography data record, comprising:

means for generating a tomography data record of a hollow organ;

means for automatically analyzing the tomography data record and determining organ sections to be assessed as critical;

means for generating a corresponding findings list entry in a findings list upon determining an organ section to be assessed as critical;

means for successively displaying various organ sections on the basis of the generated tomography data record; and means for rendering an organ section assessed as critical, after first display, as selectable for renewed display directly via the findings list.

14. The tomography workstation as claimed in claim 13, wherein the findings list is displayed during the display of the organ sections.

15. The tomography workstation as claimed in claim 13, wherein the display of a findings list entry takes place in highlighted fashion after the first display of the corresponding organ section.

16. The tomography workstation as claimed in claim 13, wherein the organ sections to be displayed are manually selectable by a user.

17. A non-transitory computer readable medium including program segments for, when executed on a computer device, causing the computer device to implement the method of claim 1.

* * * * *